United States Patent [19]
Sone et al.

[11] Patent Number: 6,121,396
[45] Date of Patent: *Sep. 19, 2000

[54] OLEFIN POLYMERIZATION CATALYST AND PROCESS FOR PRODUCING OLEFIN POLYMER

[75] Inventors: Makoto Sone; Saiki Hasegawa; Satoru Yamada; Akihiro Yano, all of Mie, Japan

[73] Assignee: Tosoh Corporation, Yamaguchi, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/548,129

[22] Filed: Oct. 25, 1995

[30] Foreign Application Priority Data

Oct. 25, 1994 [JP] Japan ..................... 6-260222

[51] Int. Cl.$^7$ ..................................... C08F 4/642
[52] U.S. Cl. ................. 526/153; 526/160; 526/161; 526/352; 526/348; 526/943; 526/348.5; 502/114; 502/152
[58] Field of Search .................. 526/126, 127, 526/160, 152

[56] References Cited

U.S. PATENT DOCUMENTS

| | | | |
|---|---|---|---|
| 5,539,066 | 7/1996 | Winter et al. | 526/160 |
| 5,710,222 | 1/1998 | Ewen et al. | 526/160 |

FOREIGN PATENT DOCUMENTS

| | | | |
|---|---|---|---|
| 500944 | 9/1992 | European Pat. Off. | 526/160 |
| 530908 | 3/1993 | European Pat. Off. | |
| 612768 | 8/1994 | European Pat. Off. | |

*Primary Examiner*—David W. Wu
*Assistant Examiner*—Caixia Lu
*Attorney, Agent, or Firm*—Sughrue, Mion, Zinn, Macpeak & Seas, PLLC

[57] ABSTRACT

A catalyst for polymerization of an olefin is provided which comprises a metallocene compound having a specified substituted fluorenyl group, and a compound capable of reacting the metallocene compound to form a cationic metallocene compound. With this compound, a high-molecular olefin polymer having narrow composition distribution and narrow molecular-weight distribution can be obtained at a polymerization temperature of not lower than 120° C.

15 Claims, No Drawings

OLEFIN POLYMERIZATION CATALYST AND PROCESS FOR PRODUCING OLEFIN POLYMER

BACKGROUND OF THE INVENTION

1. Field of the Invention

The present invention relates to an olefin polymerization catalyst comprising a metallocene compound having a substituted fluorenyl group having an electron-donating substituent on the benzo ring as one ligand, a cyclopentadienyl group as another ligand, and a hydrocarbon group, a silanediyl group, or a germanediyl group forming a bridge between the two ligands. The present invention also relates to a process for producing an olefin polymer of a high molecular weight at a high polymerization temperature of not lower than 120° C. by use of the above catalyst.

2. Description of the Related Art

In polymerization of olefin, metallocene complex catalysts are known to be highly active which comprise as fundamental constitutional components a cyclopentadienyl derivative of a transition metal such as titanium, zirconium, and hafnium (Group 4 of Periodic Table) and an aluminoxane. Such catalysts are described by J. Boor ("Ziegler-Natta Catalyst and Polymerization", Academic Press, New York (1979)) and by H. Sinn and W. Kaminsky (Adv. Organomet. Chem. 1899 (1980)). These catalysts are shown to be highly active in olefin polymerization and to be capable of forming a stereoregular polymer. JP-A-1-503788 ("JP-A" herein means "Japanese Patent Laid-Open Publication") discloses a process for producing a polyethylene of high density or an ethylene/α-olefin copolymer of relatively high density by employing the aforementioned catalyst system comprising a metallocene compound and aluminoxane at a high pressure and a high temperature.

These catalysts, however, are not employed in commercial production, mainly because of the two disadvantages below. Firstly, aluminoxane, the cocatalyst, cannot readily be prepared with high reproducibility, whereby the catalyst and the resulting polymer cannot be produced with satisfactory reproducibility. Secondary, the expensive aluminoxane has to be used in a considerably high ratio to the transition metal compound, the main catalyst, in order to obtain high catalytic activity and stability of polymerization.

The above disadvantages are offset by an ionic metallocene catalyst. JP-A-3-207704 discloses an ionic metallocene compound prepared by reaction of a metallocene compound with an ionizing ionic compound. WO-92-01723 discloses a process for polymerization of α-olefin with a catalyst system prepared by reacting a halogenated metallocene compound with an organometallic compound and further bringing the resulting product into contact with an ionizing ionic compound, and describes advantages of such a catalyst system for olefin polymerization.

JP-A-5-320246 discloses high temperature polymerization with an ionic metallocene catalyst, where the polymerization catalyst is prepared from a known complex of dicyclopentadienylzirconium dichloride, dimethylanilinium tetrakis(pentafluorophenyl)borate, and triisobutylaluminum. However, ethylene/1-octene copolymers produced with this catalyst at high temperature have a low intrinsic viscosity, namely a low molecular weight. Therefore, the polymer produced with this catalyst is presumed to be insufficient in rigidity and strength for single use for plastics.

Generally, a polymer of a higher molecular weight is obtained at a lower polymerization temperature because of slower chain transfer reactions at a lower temperature. However, in polymerization at a temperature lower than the melting temperature of the polymer, the formed polymer deposits in the reaction vessel to retard agitation and to reduce the productivity. In solution polymerization where the polymerization is conducted at a temperature higher than the melting point of the polymer, the above disadvantages are offset, and the higher temperature decreases the viscosity of the polymerization solution to increase the agitation efficiency, thereby facilitating removal of polymerization heat and control of the reaction to produce a homogeneous polymer. In high-temperature high-pressure polymerization, the larger difference between the temperature of polymerization and the temperature of the feed of raw materials will increase the olefin conversion, and will improve profit. Accordingly, for high temperature polymerization, the metallocene catalyst is being investigated which is active under high temperature conditions.

After comprehensive investigation to solve the above problems, it was found by the inventors of the present invention that a metallocene compound having a specified substituent makes practicable the production of an olefin polymer of narrow composition distribution, narrow molecular-weight distribution, and high molecular weight even under high temperature conditions of not lower than 120° C. The present invention has been completed on the basis of the above findings.

SUMMARY OF THE INVENTION

The present invention intends to provide a catalyst and a process for production of an olefin polymer having narrow composition distribution, narrow molecular weight distribution, and a high molecular weight at a polymerization temperature of 120° C. or higher.

The catalyst of the present invention for polymerization of an olefin comprises:

(a) a metallocene compound having a substituted fluorenyl group represented by General Formula (1):

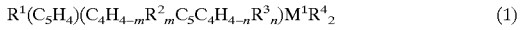

$$R^1(C_5H_4)(C_4H_{4-m}R^2{}_mC_5C_4H_{4-n}R^3{}_n)M^1R^4{}_2 \qquad (1)$$

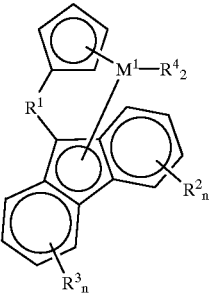

where $R^1$ is an aryl group-containing hydrocarbon, silanediyl, or germanediyl group forming a bridge between the $C_5H_4$ group and the $C_4H_{4-m}R^2{}_mC_5C_4H_{4-n}R^3{}_n$ group to increase steric rigidity of the compound of General Formula (1); $C_5C_4$ is a cyclopentadienyl group; $C_4H_{4-m}R^2{}_m C_5C_4H_{4-n}R^3{}_n$ is a substituted fluorenyl group; $R^2$ and $R^3$ are independently a substituent on the benzo ring moiety of the substituted fluorenyl group, and are independently an amino group of 1 to 20 carbons, an oxygen-containing hydrocarbon group of 1 to 20 carbons, or a halogen; $M^1$ is Ti, Zr, or Hf; each of $R^4$ is independently a hydrogen atom, a hydrocarbon group, an amino group of 1 to 20 carbons, an oxygen-containing hydrocarbon group of 1 to 20 carbons, or a halogen; m is an integer of from 0 to 4; n is an integer of from 0 to 4; and the sum of m and n is one or more; and (a) a compound which reacts with the metallocene compound to form a cationic metallocene compound. The catalyst may further comprise (c) an organometallic compound.

The process of the present invention for producing an olefin polymer is conducted by use of the above olefin polymerization catalyst.

DETAILED DESCRIPTION OF THE PREFERRED EMBODIMENT

The metallocene compound employed in the present invention is represented by General Formula (1):

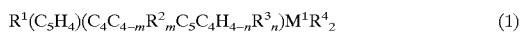

$$R^1(C_5H_4)(C_4C_{4-m}R^2{}_mC_5C_4H_{4-n}R^3{}_n)M^1R^4{}_2 \quad (1)$$

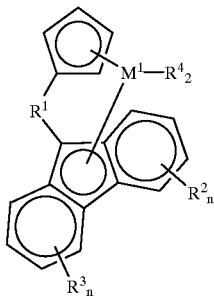

where $R^1$ is an aryl group-containing hydrocarbon, silanediyl, or germanediyl group forming a bridge between the $C_5H_4$ group and the $C_4H_{4-m}R^2{}_mC_5C_4H_{4-n}R^3{}_n$ group to raise steric rigidity of the compound of General Formula (1), including preferably arylalkylene groups, alkylsilanediyl groups, arylsilanediyl groups, alkylgermandiyl groups, and arylgermanediyl groups. Specifically, the arylalkylene groups include phenylmethylene, phenylmethylmethylene, diphenylmethylene, 1-phenylethylidene, ditolylmethylene, and dinaphthylmethylene. The alkylsilanediyl groups include dimethylsilanediyl, diethylsilanediyl, and cyclopropylsilanediyl. The arylsilanediyl groups include phenylmethylsilanediyl, diphenylsilanediyl, and ditolylsilanediyl. The alkylgermanediyl groups include dimethylgermanediyl, and diethylgermanediyl. Arylgermanediyl groups include phenylmethylgermanediyl, diphenylgermanediyl, and ditolylgermanediyl. In view of suppression of molecular vibration of the substituted fluorenyl group, or the cyclopentadienyl group as the ligands, preferably the bridge is formed by a single carbon or silicon atom between the cyclopentadienyl moiety and the 9-position of the substituted fluorenyl group, and a phenyl group derivative is bonded to the bridging atom. Such a bridging group is exemplified by diphenylmethylene, diphenylsilanediyl, ditolylmethylene, ditolylsilanediyl, dinaphthylmethylene, and dinaphthylsilanediyl.

The fluorenyl skeleton is represented by General Formula (2):

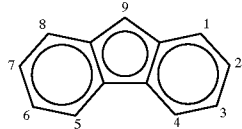

where the attached numbers shows the positions of substitution in the fluorenyl skeleton.

$R^2$ and $R^3$ are independently a substituent on the benzo ring moiety of the substituted fluorenyl group, and are an amino group of 1 to 20 carbons, an oxygen-containing hydrocarbon group of 1 to 20 carbons, or a halogen atom; preferably an amino group of 1 to 20 carbons, or an oxygen-containing hydrocarbon group of 1 to 20 carbons. Specifically, the amino group of 1 to 20 carbons includes dimethylamino, diethylamino, dipropylamino, dibutylamino, dipentylamino, dihexylamino, diheptylamino, dioctylamino, dinonylamino, didecylamino, diisopropylamino, diisobutylamino, diamylamino, diisoamylamino, diphenylamino, methylphenylamino, ethylphenylamino, ditolylamino, methyltolylamino, dibenzylamino, benzylmethylamino, dinaphthylamino, cyclopropylamino, cyclobutylamino, cyclopentylamino, and cyclohexylamino. The oxygen-containing hydrocarbon group of 1 to 20 carbons specifically includes methozy, ethoxy, propoxy, butoxy, isopropoxy, isobutoxy, phenoxy, 1-phenylmethoxy, naphthoxy, 2-methoxymethyl, and 2-methoxyethyl.

$M^1$ is Ti, Zr, or Ef.

Each of $R^4$ is independently a hydrogen atom, a hydrocarbon group such as methyl, ethyl, propyl, butyl, pentyl, hexyl, heptyl, octyl, nonyl, decyl, isopropyl, isobutyl, isopentyl, phenyl, methylphenyl, ethylphenyl, tolyl, methyltolyl, benzyl, naphthyl, cyclopropyl, cyclobutyl, cyclopentyl, and cyclohexyl; or an amino group of 1 to 20 carbons, an oxygen-containing hydrocarbon group of 1 to 20 carbons, or a halogen as mentioned for $R^2$ and $R^3$.

The symbols m and n indicate the number of the substituents in the fluorenyl group, the symbol m being an integer of from 0 to 4; and the symbol n being an integer of from 0 to 4. The sum of m and n is one or more, which means that at least one of the benzo ring moieties is substituted by a substituent $R^2$ or $R^3$.

The metallocene compound specifically includes
diphenylmethylene(cyclopentadienyl)(2-dimethyaminofluorenyl)zirconium dichloride,
diphenylmethylene(cyclopentadienyl)(2-dimethylaminofluorenyl)dimethylzirconium,
diphenylmethylene(cyclopentadienyl)(2-diisopropylaminofluorenyl)zirconium dichloride,
diphenylmethylene(cyclopentadienyl)(2-diisopropylaminofluorenyl)dimethylzirconium,
diphenylmethylene(cyclopentadienyl)(4-dimethylaminofluorenyl)zirconium dichloride,
diphenylmethylene(cyclopentadienyl)(4-dimethylaminofluorenyl)dimethylzirconium,
diphenylmethylene(cyclopentadienyl)(2-methoxyfluorenyl) zirconium dichloride,
diphenylmethylene(cyclopentadienyl)(2-methoxyfluorenyl) dimethylzirconium,
diphenylmethylene(cyclopentadienyl)(4-methoxyfluorenyl) zirconium dichloride,
diphenylmethylene(cyclopentadienyl)(4-methoxyfluorenyl) dimethylzirconium,
diphenylmethylene(cyclopentadienyl)[2,7-bis(methoxyfluorenyl)]zirconium dichloride, diphenylmethylene(cyclopentadienyl)[2,7-bis(methoxyfluorenyl)]dimethylzirconium,
diphenylmethylene(cyclopentadienyl)[2,7-bis(dimethylaminofluorenyl)]zirconium dichloride,
diphenylmethylene(cyclopentadienyl)[2,7-bis(dimethylaminofluorenyl)]dimethylzirconium,
diphenylsilanediyl(cyclopentadienyl)(2-dimethylaminofluorenyl)zirconium dichloride,
diphenylsilanediyl(cyclopentadienyl)(2-dimethylaminofluorenyl)dimethylzirconium,
diphenylsilanediyl(cyclopentadienyl)(2-diisopropylaminofluorenyl)zirconium dichloride,
diphenylsilanediyl(cyclopentadienyl)(2-diisopropylaminofluorenyl)dimethylzirconium,
diphenylsilanediyl(cyclopentadienyl)(4-dimethylaminofluorenyl)zirconium dichloride,
diphenylsilanediyl(cyclopentadienyl)(4-dimethylaminofluorenyl)dimethylzirconium,
diphenylsilanediyl(cyclopentadienyl)(2-methoxyfluorenyl)zirconium dichloride,
diphenylsilanediyl(cyclopentadienyl)(2-methoxyfluorenyl)dimethylzirconium,
diphenylsilanediyl(cyclopentadienyl)(4-methoxyfluorenyl)zirconium dichloride,
diphenylsilanediyl(cyclopentadienyl)(4-methoxyfluorenyl)dimethylzirconium,
diphenylsilanediyl(cyclopentadienyl)[2,7-bis(methoxyfluorenyl)]zirconium dichloride,
diphenylsilanediyl(cyclopentadienyl)[2,7-bis(methoxyfluorenyl)]dimethylzirconium,
diphenylsilanediyl(cyclopentadienyl)[2,7-bis(dimethylaminofluorenyl)]zirconium dichloride,
diphenylsilanediyl(cyclopentadienyl)[2,7-bis(dimethylaminofluorenyl)]dimethylzirconium;
and metallocene compounds derived by replacing the central metal, Zr, with Ti or Hf, but the metallocene compound is not limited thereto.

The compound which reacts with the metallocene compound to form a cationic metallocene compound includes protonic acids (3), Lewis acids (4), ionizing ionic compounds (5), Lewis-acidic compounds, and aluminoxanes (7) and (8).

Additionally, an organometallic compound (9) which has at least one alkyl group may be used for promoting formation of the cationic metallocene compound including alkylation and hydrogenation, and for protecting the formed cationic metallocene compound from a catalytic poison.

The protonic acid is represented by General Formula (3) below:

$$[HL^1_l][M^2R^8_4] \qquad (3)$$

where H is a proton; each of $L^1$ is independently a Lewis base; $0<l\leq 2$; $M^2$ is a boron, aluminum or gallium atom; and each of $R^8$ is independently a halogen-substituted aryl group of 6 to 20 carbons.

The Lewis acid is represented by General Formula (4):

$$[C][M^2R^8_4] \qquad (4)$$

where C is a carbonium cation or a tropylium cation; $M^2$ is a boron, aluminum or gallium atom; and each of $R^8$ is independently a halogen-substituted aryl group of 6 to 20 carbons.

The ionizing ionic compound is represented by General Formula (5):

$$[M^3L^2_r][M^2R^8_4] \qquad (5)$$

where $M^3$ is a metal cation selected from Groups 1, 2, 8, 9, 10, 11, and 12 of the Periodic Table; each of $L^2$ is independently a Lewis base, or a cyclopentadienyl group; $0\leq r \leq 2$; $M^2$ is a boron, aluminum or gallium atom; and each of $R^8$ is independently a halogen-substituted aryl group of 6 to 20 carbons.

The Lewis-acidic compound is represented by General Formula (6):

$$[M^2R^8_3] \qquad (6)$$

where $M^2$ is a boron, aluminum or gallium atom; and each of $R^8$ is independently a halogen-substituted aryl group of 6 to 20 carbons.

The protonic acid (3), Lewis acid (4), ionizing ionic compound (5), Lewis acidic compound (6), and aluminoxane (7) and (8) used as a component of the catalyst of the present invention are capable of reacting with the aforementioned metallocene compound to form a cationic metallocene compound and a counter anion therefor.

The protonic acid represented by General Formula (3) specifically includes: diethyloxonium tetrakis(pentafluorophenyl)borate, dimethyloxonium tetrakis(pentafluorophenyl)borate, tetramethyleneoxonium tetrakis(pentafluorophenyl)borate, hydronium tetrakis(pentafluorophenyl)borate, N,N-dimethylanilinium tetrakis(pentafluorophenyl)borate, tri-n-butylammonium tetrakis(pentafluorophenyl)borate, diethyloxonium tetrakis(pentafluorophenyl)aluminate, dimethyloxonium tetrakis(pentafluorophenyl)aluminate, tetramethyleneoxonium tetrakis(pentafluorophenyl)aluminate, hydronium tetrakis(pentafluorophenyl)aluminate, N,N-dimethylanilinium tetrakis(pentafluorophenyl)aluminate, and tri-n-butylammonium tetrakis(pentafluorophenyl)aluminate, but is not limited thereto.

The Lewis acid represented by General Formula (4) specifically includes: trityl tetrakis(pentafluorophenyl)borate, trityl tetrakis(pentafluorophenyl)aluminate, tropylium tetrakis(pentafluorophenyl)borate, and tropylium tetrakis(pentafluorophenyl)aluminate, but is not limited thereto.

The ionizing ionic compound represented by General Formula (5) specifically includes: lithium salts such as lithium tetrakis(pentafluorophenyl)borate, and lithium tetrakis(pentafluorophenyl)aluminate; ferrocenium salts such as ferrocenium tetrakis(pentafluorophenyl)borate, and ferrocenium tetrakis(pentafluorophenyl)aluminate; and silver salts such as silver tetrakis(pentafluorophenyl)borate, and silver tetrakis(pentafluorophenyl)aluminate; and ether complexes thereof, but is not limited thereto.

The Lewis acidic compound represented by General Formula (6) specifically includes: tris(pentafluorophenyl)borane, tris(2,3,5,6-tetrafluorophenyl)borane, tris(2,3,4,5-tetraphenylphenyl)borane, tris(3,4,5-trifluorophenyl)borane, phenyl-bis(perfluorophenyl)borane, and tris(3,4,5-trifluorophenyl)aluminum, but is not limited thereto.

The aluminoxane used in the present invention may be cyclic or linear, and is represented by General Formula (7) or (8):

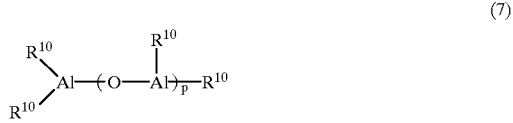

(7)

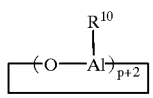

(8)

where p is an integer of 2 or more, each of $R^{10}$ is independently a hydrocarbon group, an alkylamino group, or an alkyloxy group, and at least one of $R^{10}$ is a hydrocarbon group of 1 to 20 carbons, e,g,. methyl, ethyl, propyl, butyl, octyl, isopropyl, isobutyl, decyl, dodecyl, tetradecyl, hexadecyl, etc.

The aforementioned organometallic compound employed in the present invention contains a metal of Group 1A, 2A, or 3A of Periodic Table, or Sn or Zn, and is represented by General Formula (9):

$$M^4 R^9_s \quad (9)$$

where $M^4$ is an element of groups 1, 2, or 13 of the Periodic Table, or Sn or Zn; and each of $R^9$ is independently a hydrogen atom, an alkyl or alkoxy group of 1 to 20 carbons, or an aryl, aryloxy, arylalkyl, arylalkoxy, alkylaryl, or alkylaryloxy group of 6 to 20 carbons, at least one $R^9$ being a hydrogen atom, an alkyl group of 1 to 20 carbons, or an aryl, arylalkyl, or alkylaryl group of 6 to 20 carbons; and s is equal to the oxidation number of $M^4$.

The compound represented by General Formula (9) specifically includes: trimethylaluminum, triethylaluminum, triisopropylaluminum, tri-n-propylaluminum, triisobutylaluminum, tri-n-butylaluminum, triamylaluminum, dimethylaluminum ethoxide, diethylaluminum ethoxide, diisopropylaluminum ethoxide, di-n-propylaluminum ethoxide, diisobutylaluminum ethoxide, di-n-butylaluminum ethoxide, dimethylaluminum hydride, diethylaluminum hydride, diisopropylaluminum hydride, di-n-propylaluminum hydride, diisobutylaluminum hydride, and di-n-butylaluminum hydride.

The catalyst may be prepared by mixing the metallocene compound, and the compound capable of changing the metallocene compound to a cationic metallocene compound, and additionally the organometallic compound in an inert solvent, or may be prepared by bringing the metallocene compound into contact with the organometallic compound in the presence of a polymerizing olefin in a reactor. The order of mixing the components includes several combinations. However, the method of catalyst preparation is not especially limited, provided that the cationic metallocene compound is formed.

The amount of the protonic acid, the Lewis acid, the ionizing ionic compound, or the Lewis-acidic compound to be used for preparation of the catalyst ranges preferably from 0.1 to 100 mols, more preferably from 0.5 to 30 mols, per mol of the metallocene compound. The amount of the organometallic compound used additionally is preferably not more than 100,000 mols per mol of the metallocene compound. If the organometallic compound is used in an amount larger than that, an ash removal treatment would be necessary. For production of a polymer of a high molecular weight with the catalyst of the present invention, the organometallic compound is preferably used in the smallest possible amount. The highest molecular weight of a polymer can be obtained by using, as the catalyst, only an ionizing ionic compound and a metallocene compound in which $R^4$ is an alkyl group or hydrogen. However, the organometallic compound is preferably used in an amount ranging from 1 to 1,000 mols per mol of the cationic metallocene compound in consideration of stabilization of the cationic metallocene compound and removal of a catalytic poison.

The amount of the aluminoxane used in preparation of the catalyst ranges preferably from 10 to 100,000 mols per mol of the metallocene compound, but is not especially limited. With the amount of less than 10 mols per mol thereof, the stability of the cationic metallocene compound would be low. With the amount of more than 100,000 mols per mol thereof, an ash removal treatment would be necessary. When methylaluminoxane, a typical aluminoxane, is used for the polymerization, the amount of the aluminoxane, although not especially limited, is preferably less, and is in the range of from 10 to 10,000 mols, more preferably from 10 to 1,000 mols per mol of the metallocene compound in view of the activity of the catalyst and the molecular weight of the produced polymer. Further, the organometallic compound represented by General Formula (9) may be mixed at any ratio to the aluminoxane or the metallocene compound. The ratio, however, is preferably not more than 10,000 mols per mol of the metallocene compound in order to obtain a high molecular weight of the resulting polymer.

The α-olefin of 3 or more carbons employed in the present invention includes propylene, 1-butene, 4-methyl-1-pentene, 1-hezene, 1-octene, 1-decene, 1-dodecene, 1-tetradecene, 1-hexadecene, styrene, and p-methylstyrene, and further, dienes such as butadiene, 1,5-hexadiene, 1,4-hexadiene, ethylidenenorbornene, and vinylidenenorbornene, but is limited thereto. Two or more olefins may be used in combination in the polymerization.

The method of the polymerization includes solution polymerization employing a solvent, and high-temperature high-pressure polymerization, which are known techniques.

The solution polymerization is conducted under the polymerization conditions as follows. The polymerization temperature is not lower than 120° C. The higher temperature is considered to be advantageous in polymer productivity owing to lower solution viscosity and removal of polymerization heat. Therefore, the polymerization temperature ranges preferably from 120° C. to 300° C., more preferably from 120° C. to 250° C., to obtain a high molecular weight of the resulting polymer by retarding the drop of the molecular weight caused by chain transfer reactions which proceed more rapidly at higher temperature. The polymerization pressure is not especially limited, but is preferably in the range of from atmospheric pressure to 200 kg/cm².

The high-temperature high-pressure polymerization is conducted under the polymerization conditions as follows. The polymerization temperature is not lower than 120° C. However, for the same reason as that mentioned above regarding the solution polymerization, the polymerization temperature ranges preferably from 120° C. to 300° C. in view of the productivity, more preferably from 120° C. to 250° C. for retarding the drop of the molecular weight caused by chain transfer reactions which proceed more rapidly at higher temperature. The polymerization pressure is not especially limited, but is preferably in the range of from 500 to 3500 kg/cm² in view of the productivity of the polymer. In this case, a vessel type or tubular type reactor may be used for the high-pressure process.

The present invention provides an olefin polymer having a high molecular weight, narrow molecular weight distribution, and narrow composition distribution by conducting polymerization of ethylene and/or an α-olefin by use of a metallocene catalyst of a specified structure at high temperature.

The present invention is described below in more detail by reference to examples of synthesis of the metallocene, and polymerization of olefin without limiting the invention.

The polymerization, the reaction, and the solvent purification were conducted in an inert atmosphere of purified argon or dried nitrogen throughout the experiment. The solvent for the reactions was purified, dried, and deoxygenated by known methods. The compounds reacted had been synthesized and identified by known techniques or modification thereof.

The olefin polymers obtained were subjected to measurement by gel permeation chromatography (GPC) (apparatus: Model 150C, Waters Co.) by using a column TSK-GEL GHHR-H(S) (produced by Tosoh Corp.) and o-dichlorobenzene as the eluent, at a measurement temperature of 140° C. and a sample concentration of 7 mg/10 mL (o-dichlorobenzene).

The MFR (melt flow rate) was measured according to ASTM D1238 (Condition E).

The metallocene compound was identified by $^1$H-NMR (400M) by GX-400 (JEOL, Ltd.).

REFERENCE EXAMPLE 1

Synthesis of Diphenylmethylene(cyclopentadienyl)(2-dimethylaminofluorenyl)zirconium Dichloride Into a one-liter Schlenk flask were placed 4.26 g of 2-dimethylaminofluorene and 250 mL of tetrahydrofuran. The flask was cooled to −78° C. Into the flask, 11 mL of a 1.72N n-BuLi solution in hexane was gradually added dropwise. The reaction solution was spontaneously brought to room temperature, and then cooled again to −78° C. Thereto, a solution of 5.1 g of diphenylfulvene in 250 mL of tetrahydrofuran was gradually added dropwise. The mixture was stirred vigorously overnight while the temperature thereof was allowed to rise spontaneously to room temperature. A red homogeneous reaction solution was thereby obtained. This reaction solution was washed with a saturated sodium chloride solution, and the solvent was evaporated off. The residue was purified by column chromatography to obtain 7.6 g of slightly yellowish white solid. This solid was placed in another Schlenk flask together with 250 mL of tetrahydrofuran. The mixture was cooled to −78° C. Thereto, 6.5 mL of a 1.72N n-BuLi solution in hexane was gradually added dropwise, and then the mixture was brought to room temperature. To this reaction solution, a solution of 1.15 g of zirconium tetrachloride in 100 mL of tetrahydrofuran was introduced slowly to obtain 1.15 g of intended diphenylmethylene(cyclopentadienyl)(2-dimethylaminofluorenyl)zirconium dichloride. This compound was identified by $^1$H-NMR as shown in Table 1.

REFERENCE EXAMPLE 2

Synthesis of Diphenylmethylene(cyclopentadienyl)(2-diethylaminofluorenyl)zirconium Dichloride The synthesis was conducted in the same manner as in Reference Example 1 except that 2-dimethylaminofluorene was replaced by 2-diethylaminofluorene.

REFERENCE EXAMPLE 3

Synthesis of Diphenylmethylene(cyclopentadienyl)[2,7-bis(diethylamino)fluorenyl]zirconium Dichloride The synthesis was conducted in the same manner as in Reference Example 1 except that 2-dimethylaminofluorene was replaced by 2,7-bis(diethylamino)fluorene.

REFERENCE EXAMPLE 4

Synthesis of Diphenylmethylene(cyclopentadienyl)[2,7-bis(diethylamino)fluorenyl]hafnium Dichloride The synthesis was conducted in the same manner as in Reference Example 3 except that zirconium tetrachloride was replaced by hafnium tetrachloride.

REFERENCE EXAMPLE 5

Synthesis of Diphenylmethylene(cyclopentadienyl)(2-methoxyfluorenyl)zirconium Dichloride The synthesis was conducted in the same manner as in Reference Example 1 except that 2-dimethylaminofluorene was replaced by 2-methoxyfluorene.

TABLE 1

| Reference Example | Complex/Chemical Formula | $^1$H-NMR data, δ(ppm), $^{HH}$J(Hz) |
|---|---|---|
| 1 | Diphenylmethylene(cyclopentadienyl)(2-dimethylaminofluorenyl)zirconium dichloride $(C_6H_5)_2C(C_5H_4)[2-(CH_3)_2N—C_{13}H_7]ZrCl_2$ | 2.70(s), 5.24(d, J=2.4), 5.29(s), 5.71(m), 5.85(m), 6.34(m), 6.37(d, J=8.4), 6.41(m), 6.90(m), 7.13(dd, J=9.2, 2.4), 7.20–7.45(m), 7.51(m), 7.87–7.93(m), 7.97(m) in $CDCl_3$ |
| 2 | Diphenylmethylene(cyclopentadienyl)(2-diethylaminofluorenyl)zirconium dichloride $(C_6H_5)_2C(C_5H_4)[2-(C_2H_5)_2N—C_{13}H_7]ZrCl_2$ | 0.96(t, J=7.5), 3.07(m), 5.13(d, J=2.8), 5.70 (m), 5.76(m), 6.32(m), 6.35(d, J=9.2), 6.41 (m), 6.88(td,J = 16, 1.2), 7.04(dd, J=12, 2.4), 7.21–7.52(m), 7.87–7.97(m) in $CDCl_3$ |
| 3 | Diphenylmethylene(cyclopentadienyl)[2,7-bis(diethylamino)fluorenyl]zirconium dichloride $(C_6H_5)_2C(C_5H_4)[2,7-\{(C_2H_5)_2N\}_2—C_{13}H_6]ZrCl_2$ | 0.76(t, J=7.2), 3.05(m), 5.33(d, J=2.8), 5.75 (m), 6.29(m), 6.58(m), 6.74(m), 6.83–7.07(m), 7.61(m), 7.70(m), 7.75(m) in $C_6D_6$ |
| 4 | Diphenylmethylene(cyclopentadienyl)[2,7-bis(diethylamino)fluorenyl]hafnium dichloride $(C_6H_5)_2C(C_5H_4)[2,7-(C_2H_5)_2N]_2—C_{13}H_6]HfCl_2$ | 0.90(t, J=6.8), 3.60(m), 5.27(d, J=2.8), 5.63(d, J=2.6), 6.19(t, J=3.2), 6.48(m), 6.99(dd, J=9.2, 2.8), 7.16(d, J=9.2), 7.20(tm, J=7.4), 7.32(tm, J=7.4), 7.38(tm, J= 7.4), 7.73(d, J=9.2), 7.92(m) in THF-d8 |
| 5 | Diphenylmethylene(cyclopentadienyl)(2-methoxyfluorenyl)zirconium dichloride $(C_6H_5)_2C(C_5H_4)(2-CH_3O—C_{13}H_7)ZrCl_2$ | 3.36(s), 5.70(m), 6.41(m), 6.95(m), 7.15–7.25(m), 7.29(m), 7.37(m), 7.44(m), 7.55(m), 7.87–7.98(m), 8.07(m) in $CDCl_3$ |

EXAMPLE 1

In a one-liter reactor was placed 600 mL of an aliphatic hydrocarbon (IP Solvent 1620, Idemitsu Petrochemical Co.) as the solvent. The reactor was controlled to be at a temperature of 170° C. Ethylene was fed to the reactor to keep the pressure at 20 kg/cm².

Separately, in another vessel, 1.0 μmol of diphenylmethylene(cyclopentadienyl)(2-dimethylaminofluorenyl)zirconium dichloride was dissolved in toluene. Thereto, a solution of triisobutylaluminum in toluene (triisobutylaluminum concentration: 20% by weight) was added in an amount of 100 μmols in terms of aluminum. The mixture was stirred for one hour, and was added to a solution of 1.2 μmol of N,N-dimethylanilinium tetrakis(pentafluorophenyl)borate in 1 mL of toluene. The mixture was stirred for 10 minutes. The resulting mixture was introduced into the aforementioned reactor with the aid of nitrogen pressure.

After introduction of the mixture into the reactor, the content in the reactor was heated to 170° C., and was stirred at 1500 rpm by keeping the temperature at 170° C. for 20 minutes to allow polymerization to proceed. The obtained polymer was dried in vacuo at 100° C. for 6 hours. Thereby polyethylene was obtained in a yield of 30.8 g. The MFR and other test results of the obtained polymer are shown in Table 2.

EXAMPLE 2

Polymerization was conducted in the same manner as in Example 1 except that the amount of triisobutylaluminum was changed to 250 μmol. The results are shown in Table 2.

EXAMPLE 3

Copolymerization was conducted in the same manner as in Example 2 except that 20 mL of 1-hexene was introduced subsequently to the introduction of the solvent into the reactor. The results are shown in Table 2.

COMPARATIVE EXAMPLE 1

In a one-liter reactor was placed 600 mL of an aliphatic hydrocarbon (IP Solvent 1620, Idemitsu Petrochemical Co.) as the solvent, and immediately thereto 20 mL of 1-hexene was introduced. The reactor was controlled to be at a temperature of 170° C. Ethylene was fed to the reactor to keep the pressure at 20 kg/cm².

Separately, in another vessel, 1.0 μmol of diphenylmethylene(cyclopentadienyl)(fluorenyl)zirconium dichloride was dissolved in toluene, and thereto a solution of triisobutylaluminum in toluene (triisobutylaluminum concentration: 20% by weight) was added in an amount of 250 μmols in terms of aluminum. The mixture was stirred for one hour. This mixture was added to a solution of 1.2 μmol of N,N-dimethylanilinium tetrakis(pentafluorophenyl)borate in 1 mL of toluene, and the mixture was stirred for 10 minutes. The resulting mixture was introduced into the aforementioned reactor with the aid of nitrogen pressure.

After introduction of the mixture into the reactor, the contents of the reactor were stirred at 1,500 rpm while keeping the temperature at 170° C. for 20 minutes to allow polymerization to proceed. The obtained polymer was dried in vacuo at 100° C. for 6 hours. The polymer had a molecular weight lower than the one obtained by use of the catalyst of the present invention. The results are shown in Table 2.

EXAMPLE 4

Polymerization was conducted in the same manner as in Example 1 except that the amount of trisobutylaluminum was changed to 4 mmols/L. The results are shown in Table 2.

EXAMPLE 5

Polymerization was conducted in the same manner as in Example 2 except that the triisobutylaluminum was changed to trimethylaluminum. The results are shown in Table 2.

EXAMPLE 6

Polymerization was conducted in the same manner as in Example 1 except that the amount of triiusobutylaluminum was changed to 1 mmol. The results are shown in Table 2.

EXAMPLE 7

In a one-liter reactor was placed 600 mL of an aliphatic hydrocarbon (IP Solvent 1620, Idemitsu Petrochemical Co.) as the solvent. The reactor was controlled to be at a temperature of 170° C. Ethylene was fed to the reactor to keep the pressure at 20 kg/cm².

Separately, in another vessel, 1.0 μmol of diphenylmethylene(cyclopentadienyl)(2-dimethylaminofluorenyl)zirconium dichloride was dissolved in toluene, thereto a solution of methylaluminoxane in toluene (Tosoh Akzo K.K., methylaluminoxane concentration: 20% by weight)

TABLE 2

|  | Example | | | Comparative Example | Example | | |
|---|---|---|---|---|---|---|---|
|  | 1 | 2 | 3 | 1 | 4 | 5 | 6 |
| Metallocene | A-1 | A-1 | A-1 | B-1 | A-1 | A-1 | A-1 |
| μmol | 1.0 | 1.0 | 1.0 | 1.0 | 1.0 | 1.0 | 1.0 |
| Cocatalyst a | C-1 | C-1 | C-1 | C-1 | C-1 | C-1 | C-1 |
| μmol | 1.2 | 1.2 | 1.2 | 1.2 | 1.2 | 1.2 | 1.2 |
| Cocatalyst b | TIBAL | TIBAL | TIBAL | TIBAL | TIBAL | TMAL | TMAL |
| μmol | 100 | 250 | 250 | 250 | 4000 | 250 | 1000 |
| Al/M | 100 | 250 | 250 | 250 | 4000 | 250 | 1000 |
| Polymerization temperature ° C. | 170 | 170 | 170 | 170 | 170 | 170 | 170 |
| Polymerization time min | 20 | 20 | 20 | 20 | 20 | 20 | 20 |
| Ethylene pressure kg/cm² | 20 | 20 | 20 | 20 | 20 | 20 | 20 |
| 1-Hexene mL | 0 | 0 | 20 | 20 | 0 | 0 | 0 |
| Ethylidenenorbornene mL | 0 | 0 | 0 | 0 | 0 | 0 | 0 |
| Solvent mL | 600 | 600 | 600 | 600 | 600 | 600 | 600 |
| Yield g | 30.8 | 31.6 | 43.4 | 22.0 | 20.5 | 8.6 | 20.4 |
| MFR g/10 min | 0.09 | 0.23 | 0.39 | 4.80 | 20.5 | 1.07 | 1.63 |
| Mw/Mn | 2.0 | 2.0 | 2.0 | 2.2 | 2.1 | 2.0 | 1.9 |

TABLE 2-continued

|  | Example | | | Comparative Example | Example | | |
| --- | --- | --- | --- | --- | --- | --- | --- |
|  | 1 | 2 | 3 | 1 | 4 | 5 | 6 |
| Density g/cc | 0.945 | 0.947 | 0.927 | 0.921 | 0.967 | 0.955 | 0.957 |
| Melting point ° C. | 136 | 136 | 122 | 119 | 137 | 137 | 137 |

A-1: Diphenylmethylene(cyclopentadienyl) (2-dimethylaminofluorenyl)zirconium dichloride
B-1: Diphenylmethylene(cyclopentadienyl) (fluorenyl)zirconium dichloride
C-1: Dimethylanilinium tetrakis(pentafluorophenyl)borate
TIBAL: Triisobutylaluminum
TMAL: Trimethylaluminum was added in an amount of 1,000 μmols in terms of aluminum, and the total volume was adjusted to 10 mL by addition of toluene. The mixture was stirred for one hour. The resulting mixture was introduced into the aforementioned reactor with the aid of nitrogen pressure.

After introduction of the mixture into the reactor, the content in the reactor was stirred at 1,500 rpm while keeping the temperature at 170° C. for 20 minutes to allow polymerization to proceed. The obtained polymer was dried in vacuo at 100° C. for 6 hours. Polyethylene was thereby obtained in a yield of 30.6 g. The MFR and other test results of the obtained polymer are shown in Table 3.

COMPARATIVE EXAMPLE 2

In a one-liter reactor, was placed 600 mL of an aliphatic hydrocarbon (IP Solvent 1620, Idemitsu Petrochemical Co.) as the solvent. The reactor was controlled to be at a temperature of 170° C. Ethylene was fed to the reactor to keep the pressure at 20 kg/cm$^2$.

Separately, in another vessel, 1.0 μmol of diphenylmethylene(cyclopentadienyl)(fluorenyl)zirconium dichloride was dissolved in toluene, thereto a solution of methylaluminoxane in toluene (Tosoh Akzo K.K., methylaluminoxane concentration: 20% by weight) was added in an amount of 1,000 μmols in terms of aluminum, and the total volume was adjusted to 10 mL by addition of toluene. The mixture was stirred for one hour. The resulting mixture was introduced into the aforementioned reactor with the aid of nitrogen pressure.

After introduction of the mixture into the reactor, the content in the reactor was stirred at 1,500 rpm while keeping the temperature at 170° C. for 20 minutes to allow polymerization to proceed. The obtained polymer was dried in vacuo at 100° C. for 6 hours. Polyethylene was thereby obtained in a yield of 24.3 g. The MFR and other test results of the obtained polymer are shown in Table 3.

EXAMPLE 8

Copolymerization was conducted in the same manner as in Example 1 except that 20 mL of 1-hexene and 10 mL of ethylidenenorbornene were introduced subsequently to the introduction of the solvent into the reactor. The results are shown in Table 3.

EXAMPLE 9

Polymerization was conducted in the same manner as in Example 7 except that the amount of the methylaluminoxane was changed to 4 mmols. The results are shown in Table 3.

EXAMPLE 10

Polymerization was conducted in the same manner as in Example 7 except that the amount of the methylaluminoxane

TABLE 3

|  | Example | Comparative Example | Example | | | | |
| --- | --- | --- | --- | --- | --- | --- | --- |
|  | 7 | 2 | 8 | 9 | 10 | 11 | 12 |
| Metallocene | A-1 | B-1 | A-1 | A-1 | A-1 | A-3 | A-3 |
| μmol | 1.0 | 1.0 | 1.0 | 1.0 | 1.0 | 1.0 | 1.0 |
| Cocatalyst a | D-1 | D-1 | C-1 | D-1 | D-1 | C-1 | C-1 |
| μmol | 1000 | 1000 | 1.2 | 4000 | 10000 | 1.2 | 1.2 |
| Cocatalyst b | — | — | TIBAL | — | — | TIBAL | TIBAL |
| μmol | — | — | 100 | — | — | 100 | 4000 |
| Al/M | 1000 | 100 | 100 | 4000 | 10000 | 100 | 4000 |
| Polymerization temperature ° C. | 170 | 170 | 170 | 170 | 170 | 170 | 170 |
| Polymerization time min | 20 | 20 | 20 | 20 | 20 | 20 | 20 |
| Ethylene pressure kg/cm$^2$ | 20 | 20 | 20 | 20 | 20 | 20 | 20 |
| 1-Hexene mL | 0 | 0 | 20 | 0 | 0 | 0 | 0 |
| Ethylidenenorbornene mL | 0 | 0 | 20 | 0 | 0 | 0 | 0 |
| Solvent mL | 600 | 600 | 600 | 600 | 600 | 600 | 600 |
| Yield g | 30.6 | 24.3 | 34.9 | 54.3 | 73.0 | 16.0 | 11.0 |
| MFR g/10 min | 0.41 | 1.00 | 0.02 | 31.0 | 440 | <0.01 | 32.5 |
| Mw/Mn | 1.9 | 2.3 | 2.0 | 2.0 | 2.3 | — | 1.9 |

TABLE 3-continued

|  | Example | Comparative Example | Example | | | | |
|---|---|---|---|---|---|---|---|
|  | 7 | 2 | 8 | 9 | 10 | 11 | 12 |
| Density g/cc | 0.950 | 0.957 | 0.910 | 0.966 | 0.970 | 0.945 | 0.957 |
| Melting point ° C. | 137 | 137 | 100 | 138 | 137 | 137 | 137 |

A-1: Diphenylmethylene(cyclopentadienyl) (2-dimethylaminofluorenyl)zirconium dichloride
A-3: Diphenylmethylene(cyclopentadienyl) [2,7-bis(diethylamino)fluorenyl]zirconium dichloride
C-1: Dimethylanilinium tetrakis(pentafluorophenyl)borate
D-1: Methylaluminoxane
TIBAL: Triisobutylaluminum was changed to 10 mmols. The results are shown in Table 3.

EXAMPLE 11

Polymerization was conducted in the same manner as in Example 1 except that diphenylmethylene (cyclopentadienyl)(2-dimethylaminofluorenyl)zirconium dichloride was replaced by diphenylmethylene (cyclopentadienyl)[2,7-bis(diethylamino)fluorenyl] zirconium dichloride. The results are shown in Table 3.

EXAMPLE 12

Polymerization was conducted in the same manner as in Example 4 except that diphenylmethylene (cyclopentadienyl)(2-dimethylaminofluorenyl)zirconium dichloride was replaced by diphenylmethylene (cyclopentadienyl)[2,7-bis(diethylamino)fluorenyl] zirconium dichloride. The results are shown in Table 3.

EXAMPLE 13

Copolymerization was conducted in the same manner as in Example 1 except that 20 mL of 1-hexene was introduced subsequently to the introduction of the solvent into the reactor and the polymerization temperature was changed to 200° C. The results are shown in Table 4.

EXAMPLE 14

Copolymerization was conducted in the same manner as in Example 13 except that diphenylmethylene (cyclopentadienyl)(2-dimethylaminofluorenyl)zirconium dichloride was replaced by diphenylmethylene (cyclopentadienyl)(2-diethylaminofluorenyl)zirconium dichloride. The results are shown in Table 4.

EXAMPLE 15

Polymerization was conducted in the same manner as in Example 1 except that diphenylmethylene (cyclopentadienyl)(2-dimethylaminofluorenyl)zirconium dichloride was replaced by diphenylmethylene (cyclopentadienyl)[2,7-bis(diethylamino)fluorenyl] zirconium dichloride and the polymerization temperature was changed to 200° C. The results are shown in Table 4.

EXAMPLE 16

Copolymerization was conducted in the same manner as in Example 13 except that diphenylmethylene (cyclopentadienyl)(2-dimethylaminofluorenyl)zirconium dichloride was replaced by diphenylmethylene (cyclopentadienyl)[2,7-bis(diethylamino)fluorenyl]hafnium dichloride. The results are shown in Table 4.

EXAMPLE 17

A toluene solution of a catalyst system comprising 650 μmmols/L of diphenylmethylene(cyclopentadienyl)(2-dimethylaminofluorenyl)zirconium dichloride, 162.5 mmols/L of triisobutylaluminum, and 780 μm/L of N,N-dimethylanilinium

TABLE 4

|  | Example | | | |
|---|---|---|---|---|
|  | 13 | 14 | 15 | 16 |
| Metallocene | A-1 | A-2 | A-3 | A-4 |
| μmol | 1.0 | 1.0 | 1.0 | 1.0 |
| Cocatalyst a | C-1 | C-1 | C-1 | C-1 |
| μmol | 1.2 | 1.2 | 1.2 | 1.2 |
| Cocatalyst b | TIBAL | TIBAL | TIBAL | TIBAL |
| μmol | 100 | 100 | 100 | 100 |
| Al/M | 100 | 100 | 100 | 100 |
| Polymerization temperature ° C. | 200 | 200 | 200 | 200 |
| Polymerization time min | 20 | 20 | 20 | 20 |
| Ethylene pressure kg/cm² | 20 | 20 | 20 | 20 |
| 1-Hexene mL | 20 | 20 | 0 | 20 |
| Ethylidenenorbornene mL | 0 | 0 | 0 | 0 |
| Solvent mL | 600 | 600 | 600 | 600 |
| Yield g | 33.0 | 25.0 | 8.0 | 6.0 |
| MFR g/10 min | 2.17 | 0.76 | <0.01 | <0.01 |
| Mw/Mn | 2.0 | 2.0 | — | — |
| Density g/cc | 0.928 | 0.927 | — | — |
| Melting point ° C. | 125 | 125 | — | — |

A-1: Diphenylmethylene(cyclopentadienyl) (2-dimethylaminofluorenyl) zirconium dichloride
A-2: Diphenylmethylene(cyclopentadienyl) (2-diethylaminofluorenyl) zirconium dichloride
A-3: Diphenylmethylene(cyclopentadienyl) [2,7-bis(diethylamino) fluorenyl]zirconium dichloride
A-4: Diphenylmethylene(cyclopentadienyl) [2,7-bis(diethylamino) fluorenyl]hafnium dichloride
C-1: Dimethylanilinium tetrakis(pentafluorophenyl)borate
TIBAL: Triisobutylaluminum tetrakis(pentafluorophenyl)borate was introduced into a high-pressure reaction vessel. Thereto, ethylene and 1-hexene were fed continuously at an ethylene pressure of 900 kg/cm² and a 1-hexene concentration of 32 mol %, and polymerization was conducted continuously at a temperature of 200° C.

Consequently, a polymer was obtained in a yield of 157 kg per mmol of zirconium. The obtained polymer was found to have an MFR of 1.3 g/10 min, and a density of 0.924 g/cc. The results are shown in Table 5.

COMPARATIVE EXAMPLE 3

Copolymerization was conducted in the same manner as in Example 17 except that diphenylmethylene (cyclopentadienyl)(2-dimethylaminofluoredyl)zirconium dichloride was replaced by diphenylmethylene (cyclopentadienyl)(fluorenyl)zirconium dichloride. The results are shown in Table 5. The obtained polymer had low molecular weight as indicated by the MFR of 9.3 g/10 min in comparison with the polymer of Example 17.

EXAMPLE 18

Copolymerization was conducted in the same manner as in example 17 except that the 1-hexene concentration was changed to 36 mol % and the polymerization temperature was changed to 210° C. The results are shown in Table 5.

TABLE 5

|  | Example 17 | Comparative Example 3 | Example 18 | Comparative Example 4 |
|---|---|---|---|---|
| Metallocene | A-1 | B-1 | A-1 | B-1 |
| Cocatalyst a | C-1 | C-1 | C-1 | C-1 |
| Cocatalyst b | TIBAL | TIBAL | TIBAL | TIBAL |
| Polymerization temperature ° C. | 200 | 200 | 210 | 210 |
| 1-Hexene concentration mol % | 32 | 32 | 36 | 36 |
| Ethylene pressure kg/cm$^2$ | 900 | 900 | 900 | 900 |
| Activity kg/mmol Zr | 157 | 343 | 87 | 102 |
| MFR g/10 min | 1.3 | 9.3 | 2.0 | 16.9 |
| Density g/cc | 0.924 | 0.921 | 0.922 | 0.921 |

A-1: Diphenylemethylene(cyclopentadienyl) (2-dimethylaminofluorenyl) zirconium dichloride
B-1: Diphenylmethylene(cyclopentadienyl) (fluorenyl)zirconium dichloride
C-1: Dimethylanilinium tetrakis(pentafluorophenyl)borate
TIBAL: Triisobutylaluminum

COMPARATIVE EXAMPLE 4

Copolymerization was conducted in the same manner as in Comparative Example 3 except that the 1-hexene concentration was changed to 36 mol % and the polymerization temperature was changed to 210° C. The results are shown in Table 5.

EXAMPLE 19

Copolymerization was conducted in the same manner as in Example 3 except that diphenylmethylene (cyclopentadienyl)(2-dimethylaminofluorenyl)zirconium dichloride was replaced by diphenylmethylene (cyclopentadienyl)(2-methoxyfluorenyl)zirconium dichloride. The results are shown in Table 6.

EXAMPLE 20

Copolymerization was conducted in the same manner as in Example 3 except that diphenylmethylene (cyclopentadienyl)(2-dimethylaminofluorenyl)zirconium dichloride was replaced by diphenylmethylene (cyclopentadienyl)(2-methoxyfluorenyl)zirconium dichloride and the polymerization temperature was changed to 200° C. The results are shown in Table 6.

EXAMPLE 21

Copolymerization was conducted in the same manner as in Example 3 except that diphenylmethylene (cyclopentadienyl)(2-dimethylaminofluorenyl)zirconium dichloride was replaced by diphenylmethylene (cyclopentadienyl)(2-methoxyfluorenyl)zirconium dichloride, and the amount of N,N-dimethylanilinium tetrakis(pentafluorophenyl)borate was changed to 2.0 μmols. The results are shown in Table 6.

EXAMPLE 22

Copolymerization was conducted in the same manner as in Example 3 except that diphenylmethylene (cyclopentadienyl)(2-dimethylaminofluorenyl)zirconium dichloride was replaced by diphenylmethylene (cyclopentadienyl)(2-methoxyfluorenyl)zirconium dichloride, the amount of N,N-dimethylanilinium tetrakis (pentafluorophenyl)borate was changed to 2.0 μmols, and the polymerization temperature was changed to 200° C. The results are shown in Table 6.

TABLE 6

|  | Example | | | |
|---|---|---|---|---|
|  | 19 | 20 | 21 | 22 |
| Metallocene | A-5 | A-5 | A-5 | A-5 |
| μmol | 1.0 | 1.0 | 1.0 | 1.0 |
| Cocatalyst a | C-1 | C-1 | C-1 | C-1 |
| μmol | 1.2 | 1.2 | 2.0 | 2.0 |
| Cocatalyst b | TIBAL | TIBAL | TIBAL | TIBAL |
| μmol | 250 | 250 | 250 | 250 |
| Al/M | 250 | 250 | 250 | 250 |
| Polymerization temperature ° C. | 170 | 200 | 170 | 200 |
| Polymerization time min | 20 | 20 | 20 | 20 |
| Ethylene pressure kg/cm$^2$ | 20 | 20 | 20 | 20 |
| 1-Hexene mL | 20 | 20 | 20 | 20 |
| Ethylidenenorbornene mL | 0 | 0 | 0 | 0 |
| Solvent mL | 600 | 600 | 600 | 600 |
| Yield g | 72.4 | 28.0 | 68.0 | 48.0 |
| MFR g/10 min | 0.70 | 5.60 | 1.99 | 6.68 |
| Mw/Mn | 1.9 | — | — | — |
| Melting point ° C. | 120 | 119 | 119 | 120 |

A-5: Diphenylmethylene(cyclopentadienyl) (2-methoxyfluorenyl)zirconium chloride
C-1: Aimethylanilinium tetrakis(pentafluorophenyl)borate
TIBAL: Triisobutylaluminum

What is claimed is:

1. A process for producing an olefin polymer or copolymer which comprises homopolymerizing ethylene or copolymerizing ethylene and an alpha-olefin of three or more carbon atoms at a polymerization temperature of not lower than 120° C. using a catalyst which comprises a metallocene compound and a compound which reacts with the metallocene compound to form a cationic metallocene compound, wherein the metallocene compound is:

a metallocene compound having a substituted fluorenyl group represented by General Formula (1):

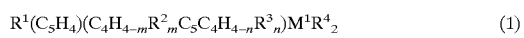

$$R^1(C_5H_4)(C_4H_{4-m}R^2{}_mC_5C_4H_{4-n}R^3{}_n)M^1R^4{}_2 \qquad (1)$$

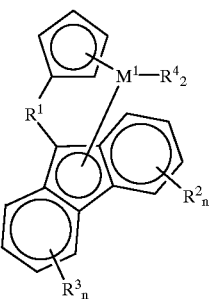

where $R^1$ is an aryl group-containing hydrocarbon arylalkylene group forming a bridge between the $C_5H_4$ group and the $C_4H_{4-m}R^2{}_mC_5C_4H_{4-n}R^3{}_n$ group to increase steric rigidity of the compound of General Formula (1); $C_5H_4$ is a cyclopentadienyl group; $(C_4H_{4-m}R^2{}_mC_5C_4H_{4-n}R^3{}_n)$ is a substituted fluorenyl group; $R^2$ and $R^3$ are independently a substituent on the benzo ring moiety of the substituted fluorenyl group, and are independently an amino group of 1 to 20 carbons or an alkoxy group of 1 to 20 carbons, $M^1$ is Zr or Hf; each of $R^4$ is independently a hydrogen atom, a hydrocarbon group, an amino group of 1 to 20 carbons, an oxygen-containing hydrocarbon group of 1 to 20 carbons, or a halogen; m is an integer of from 0 to 4; n is an integer of from 0 to 4; and the sum of m and n is one or more, wherein the substituted fluorenyl group is substituted at at least one of the 2-position, 4- position or the 7- position thereof, wherein the compound which reacts with the metallocene compound to form a cationic metallocene compound is an aluminoxane, a protonic acid, a Lewis acid, an ionizing ionic compound or a Lewis acidic compound, which compound which reacts with the metallocene compound to form a cationic metallocene compound yields a counter anion to the metallocene, wherein an organoaluminum compound is further present, wherein the amount of aluminoxane as methyl aluminoxane is 10–10,000 mol/mol of the metallocene compound, the amount of the organoaluminum compound is 1–1,000 mol/mol of the metallocene compound, and wherein the amount of the protonic acid, Lewis acid, ionizing ionic compound or Lewis acidic compound is from 0.1 to 100 mol/mol of the metallocene compound.

2. A process for producing an olefind polymer or copolymer as claimed in claim 1, wherein said aluminoxane is represented by General Formula (7) or (8):

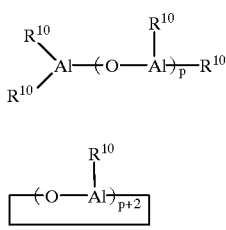

(7)

(8)

where p is an integer of 2 or more, each of $R^{10}$ is independently a hydrocarbon group, an alkylamino group, or a alkyloxy group, and at least one of $R^{10}$ is a hydrocarbon group of 1 to 20 carbons.

3. A process for producing an olefin polymer or copolymer as claimed in claim 1 which further comprises the use of an organometallic compound, wherein said organometallic compound is represented by General Formula (9):

$$M^4R^9_s \qquad (9)$$

where $M^4$ is an element of groups 1,2, or 13 of the Periodic Table, or Sn or Zn; and each of $R^9$ is independently a hydrogen atom, an alkyl or alkoxy group of 1 to 20 carbons, or an aryl, aryloxy, arylalkyl, arylalkoxy, alkylaryl, or alkylaryloxy group of 6 to 20 carbons, at least one $R^9$ being a hydrogen atom, an alkyl group of 1 to 20 carbons, or any aryl, arylalkyl, or alkylaryl group of 6 to 20 carbons; and s is equal to the oxidation number of $M^4$.

4. A process for producing an olefin polymer or copolymer as claimed in claim 1, wherein said protonic acid is represented by General Formula (3) below:

$$[HL^1_l][M^2R^8_4] \qquad (3)$$

where H is a proton; each of $L^1$ is independently a Lewis base; $0<l\leq2$; $M^2$ is a boron, aluminum or gallium atom; and each of $R^8$ is independently a halogen-substituted aryl group of 6 to 20 carbons.

5. A process for producing an olefin polymer or copolymer as claimed in claim 1, wherein said Lewis acid is represented by General Formula (4):

$$[C][M^2R^8_4] \qquad (4)$$

where C is a carbonium cation or a tropylium cation; $M^2$ is a boron, aluminum or gallium atom; and each of $R^8$ is independently a halogen-substituted aryl group of 6 to 20 carbons.

6. A process for producing an olefin polymer or copolymer as claimed in claim 1, wherein said ionizing ionic compound is represent by General Formula (5):

$$[M^3L^2_r][M^2R^8_4] \qquad (5)$$

where $M^3$ is a metal cation selected from Groups 1, 2, 8, 9, 10, 11, and 12 of the Periodic Table; each of $L^2$ is independently a Lewis base, or a cyclopentadienyl group; $0\leq r\leq 2$; $M^2$ is a boron, aluminum or gallium atom; and each of $R^8$ is independently a halogen-substituted aryl group of 6 to 20 carbons.

7. A process for producing an olefin polymer or copolymer as claimed in claim 1, wherein said Lewis acidic compound is represented by General Formula (6):

$$[M^2R^8_3] \qquad (6)$$

where $M^2$ is a boron, aluminum or gallium atom; and each of $R^8$ is independently a halogen-substituted aryl group of 6 to 20 carbons.

8. A process for producing an olefin polymer or copolymer as claimed in claim 1, wherein said organoaluminum compound is represented by General Formula (9):

$$M^4R^9_s \qquad (9)$$

where $M^4$ is aluminum; and each of $R^9$ is independently a hydrogen atom, an alkyl or alkoxy group of 1 to 20 carbons, or an aryl, aryloxy, arylalkyl, arylalkoxy, alkylaryl, or alkylaryloxy group of 6 to 20 carbons, at least one $R^9$ being a hydrogen atom, an alkyl group of 1 to 20 carbons, or an aryl, arylalkyl, or alkylaryl group of 6 to 20 carbons; and s is equal to the oxidation number of $M^4$.

9. A process for producing an olefin polymer or copolymer as claimed in claim 1, wherein the olefin polymer is polyethylene.

10. A process for producing an olefin polymer or copolymer as claimed in claim 1, wherein the copolymer is the copolymer of ethylene and said alpha-olefin.

11. A process for producing an olefin polymer or copolymer as claimed in claim 1, wherein said copolymer is a copolymer of ethylene, an alpha-olefin and a diene.

12. A process for producing an olefin polymer or copolymer as claimed in claim 1, wherein said olefin polymer or copolymer has a density of 0.91 g/cm or more.

13. A process for producing an olefin polymer or copolymer as claimed in claim 1, wherein $R^2$ and $R^3$ are independently substituents selected from the group consisting of 2-dimethylamino-,
2-diisopropylamino-,
4-dimethylamino-,
2-methoxyl-,
4-methoxyl-,
2,7-bis (methoxy)-,
2,7-bis (dimethylamino)-,
2-diethylamino-, and
2,7-bis (diethylamino)-.

14. A process for producing an olefin polymer or copolymer as claimed in claim 1, wherein $R^2$ and $R^3$ are 2-dimethylamino.

15. A process for producing an ethylene/diene copolymer which comprises copolymerizing ethylene and a diene at a polymerization temperature of not lower than 120° C. using a catalyst which comprises a metallocene compound and a compound which reacts with the metallocene compound to form a cationic metallocene compound, wherein the metallocene compound is:

a metallocene compound having a substituted fluorenyl group represented by General Formula (1):

$$R^1(C_5H_4(C_4H_{4-m}R^2{}_mC_5C_4H_{4-n})R^3{}_n)M^1R^4{}_2 \qquad (1)$$

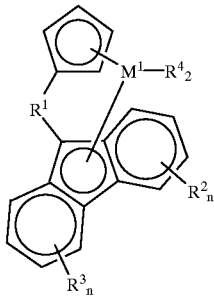

where $R^1$ is an aryl group-containing hydrocarbon arylalkylene group forming a bridge between the $C_5H_4$ group and the $C_4H_{4-m}R^2{}_mC_5C_4H_{4-n}R^3{}_n$ group to increase steric rigidity of the compound of General Formula (1); $C_5H_4$ is a cyclopentadienyl group; $(C_4H_{4-m}R^2{}_mC_5C_4H_{4-n}R^3{}_n)$ is a substituted fluorenyl group; $R_2$ and $R_3$ are independently a substituent on the benzo ring moiety of the substituted fluorenyl group, and are independently an amino group of 1 to 20 carbons or an alkoxy group of 1 to 20 carbons, M1 is Zr or Hf; each of $R^4$ is independently a hydrogen atom, a hydrocarbon group, an amino group of 1 to 20 carbons, an oxygen-containing hydrocarbon group of 1 to 20 carbons, or a halogen; n is an integer of from 0 to 4; n is an integer of from 0 to 4; and the sum of m and n is one or more, wherein the substituted fluorenyl group is substituted at at least one of the 2-position, 4-position or the 7-position thereof, wherein the compound which reacts with the metallocene compound to form a cationic metallocene compound is an aluminoxane, a protonic acid, a Lewis acid, an ionizing ionic compound or a Lewis acidic compound, which compound which reacts with the metallocene compound to form a cationic metallocene compound yields a counter anion to the metallocene, wherein an organoaluminum compound is further present, wherein the amount of aluminoxane as methyl aluminoxane is 10–10,000 mol/mol of the metallocene compound, the amount of the organoaluminum compound is 1–1,000 mol/mol of the metallocene compound, and wherein the amount of the protonic acid, Lewis acid, ionizing ionic compound or Lewis acidic compound is from 0.1 to 100 mol/mol of the metallocene compound.

* * * * *